United States Patent [19]

Grosch et al.

[11] Patent Number: 6,008,389
[45] Date of Patent: Dec. 28, 1999

[54] OXIDATION CATALYST AND PROCESS FOR THE PRODUCTION OF EPOXIDES FROM OLEFINES, HYDROGEN AND OXYGEN USING SAID OXIDATION CATALYST

[75] Inventors: Georg Heinrich Grosch, Bad Dürkheim; Ulrich Müller, Neustadt; Michael Schulz, Ludwigshafen; Norbert Rieber, Mannheim; Harald Würz, Maikammer, all of Germany

[73] Assignee: BASF Aktiengesellschaft, Ludwigshafen, Germany

[21] Appl. No.: 09/147,383

[22] PCT Filed: May 30, 1997

[86] PCT No.: PCT/EP97/02821

§ 371 Date: Dec. 14, 1998

§ 102(e) Date: Dec. 14, 1998

[87] PCT Pub. No.: WO97/47386

PCT Pub. Date: Dec. 18, 1997

[30] Foreign Application Priority Data

Jun. 13, 1996 [DE] Germany ............. 196 23 609

[51] Int. Cl.$^6$ .......... C07D 301/06; B01J 21/16; B01J 23/52; B01J 23/66; B01J 29/04
[52] U.S. Cl. ............. 549/533; 502/66; 502/242; 502/243; 502/261; 502/263
[58] Field of Search ............ 549/533; 502/66, 502/242, 243, 261, 262

[56] References Cited

FOREIGN PATENT DOCUMENTS

| 0 229 295 | 7/1987 | European Pat. Off. . |
|---|---|---|
| 0 311 983 | 10/1988 | European Pat. Off. . |
| 325 053 | 7/1989 | European Pat. Off. . |
| 0 326 759 | 8/1989 | European Pat. Off. . |
| 0 405 978 | 6/1990 | European Pat. Off. . |
| 0 640 598 | 3/1995 | European Pat. Off. . |
| 44 25 672 | 1/1996 | Germany . |
| 44 35 239 | 4/1996 | Germany . |
| 4-352771 | 12/1992 | Japan . |

*Primary Examiner*—Ba K. Trinh
*Attorney, Agent, or Firm*—Oblon, Spivak, McClelland, Maier & Neustadt, P.C.

[57] ABSTRACT

An oxidation catalyst based on titanium silicalites or vanadium silicalites having a zeolite structure and containing from 0.01 to 30% by weight of one or more noble metals selected from the group consisting of ruthenium, rhodium, palladium, osmium, iridium, platinum, rhenium, gold and silver has been molded by a compacting shaping process.

This oxidation catalyst is used for the preparation of epoxides, in particular propylene oxide, from olefins, hydrogen and oxygen.

10 Claims, No Drawings

OXIDATION CATALYST AND PROCESS FOR THE PRODUCTION OF EPOXIDES FROM OLEFINES, HYDROGEN AND OXYGEN USING SAID OXIDATION CATALYST

This application is a 371 of PCT/EP97/02821 dated May 30, 1997.

Oxidation catalyst and preparation of epoxides from olefins, hydrogen and oxygen using the oxidation catalyst The present invention relates to a novel oxidation catalyst based on titanium silicalites or vanadium silicalites having a zeolite structure and containing noble metals, and a process for the preparation of epoxides from olefins, hydrogen and oxygen using this oxidation catalyst.

Oxidation catalysts containing noble metals and based on titanium silicalites or vanadium silicalites having a zeolite structure and a process for the preparation of epoxides from olefins, hydrogen and oxygen using these oxidation catalysts are disclosed in WO-A 96/02323. There, the catalysts are used in the form of crystalline powder.

However, such oxidation catalysts of the prior art have disadvantages. When unmolded epoxidation catalysts are used, they are too fine-particled and therefore give rise to mechanical problems, for example when they are being separated off.

It is an object of the present invention to provide epoxidation catalysts which no longer have the disadvantages of the prior art.

We have found that this object is achieved by an oxidation catalyst based on titanium silicalites or vanadium silicalites having a zeolite structure and containing from 0.01 to 30% by weight of one or more noble metals selected from the group consisting of ruthenium, rhodium, palladium, osmium, iridium, platinum, rhenium, gold and silver, wherein the oxidation catalyst has been molded by a compacting shaping process.

Compacting shaping processes which may be used are in principle all methods for appropriate shaping, such as those which are usual for catalysts. Processes in which the shaping is effected by extrusion in conventional extruders, for example to give extrudates having a diameter of, usually, from 1 to 10 mm, in particular from 2 to 5 mm, are preferred. If binders and/or assistants are required, the extrusion is advantageously preceded by a mixing or kneading process. If necessary, the extrusion may be followed by a calcination step. The extrudates obtained are, if desired, comminuted, preferably to give granules or chips having a particle diameter of from 0.5 to 5 mm, in particular from 0.5 to 2 mm. These granules or these chips and also catalyst moldings produced by other methods contain virtually no particles finer than those having a minimum particle diameter of 0.5 mm.

In a preferred embodiment, the novel molded oxidation catalyst contains up to 10% by weight, based on the total mass of the catalyst, of a binder. Particularly preferred binder contents are from 0.1 to 7, in particular from 1 to 5, % by weight. Suitable binders are in principle all compounds used for such purposes; compounds, in particular oxides, of silicon, of aluminum, of boron, of phosphorus, of zirconium and/or of titanium are preferred. Silica is of particular interest as a binder, and the $SiO_2$ may be introduced into the shaping step in the form of silica sol or in the form of tetraalkoxysilanes. Oxides of magnesium and of beryllium and clays, for example montmorillonites, kaolins, bentonites, halloysites, dickites, nacrites and ananxites, may also be used as binders.

Examples of assistants for the compacting shaping processes are extrusion assistants, a conventional extrusion assistant being methylcellulose. Such agents are, as a rule, completely combusted in a downstream calcination step.

The molded oxidation catalysts prepared in this manner have a high mass-specific activity and hardness and abrasion resistance sufficient for all reaction procedures and reactor types.

The molded oxidation catalysts are based on titanium silicalites or vanadium silicalites having a zeolite structure. It is known that zeolites are crystalline aluminosilicates having ordered channel and cage structures whose pore orifices are in the range of micropores, which are smaller than 0.9 nm. The network of such zeolites is composed of $SiO_4$ and $AlO_4$ tetrahedra, which are linked via common oxygen bridges. A review of the known structures is given, for example, in W. M. Meier and D. H. Olson, Atlas of Zeolite Structure Types, Butterworth, 2nd Ed., London 1987.

Zeolites which contain no aluminum and in which some of the Si(IV) in the silicate lattice is replaced by titanium as Ti(IV) are also known. These titanium zeolites, in particular those having a crystal structure of the MFI type, and possibilities for their preparation are described, for example in EP-A 311 983 or EP-A 405 978. In addition to silicon and titanium, such materials may also contain additional elements, such as aluminum, zirconium, tin, iron, cobalt, nickel, gallium, boron or small amounts of fluorine.

In the novel oxidation catalyst, some or all of the titanium of the zeolite may be replaced by vanadium. The molar ratio of titanium and/or vanadium to the sum of silicon and titanium and/or vanadium is as a rule from 0.01:1 to 0.1:1.

It is known that titanium zeolites having an MFI structure can be identified by a certain pattern in their X-ray diffraction patterns and additionally by means of a skeletal vibration band in the infrared range (IR) at about 960 $cm^{-1}$ and thus differ from alkali metal titanates or crystalline and amorphous $TiO_2$ phases.

Typically, the stated titanium zeolites and also vanadium zeolites are prepared by reacting an aqueous mixture comprising an $SiO_2$ source, a titanium or vanadium source, such as titanium dioxide or a corresponding vanadium oxide, and a nitrogen-containing organic base (template compound), eg. tetrapropylammonium hydroxide, with or without the addition of alkali metal compounds, in a pressure-resistant container at elevated temperatures over a period of several hours or a few days, the crystalline product being formed. This is filtered off, washed, dried and calcined at elevated temperatures to remove the organic nitrogen base. In the powder thus obtained, the titanium or the vanadium is present at least partly within the zeolite skeleton, in varying proportions with four-, five- or six-fold coordination. To improve the catalytic behavior, a repeated wash treatment with hydrogen peroxide solution containing sulfuric acid may be carried out subsequently, after which the titanium zeolite or vanadium zeolite powder must again be dried and calcined; this may be followed by treatment with alkali metal compounds to convert the zeolite from the H form into the cationic form. The titanium zeolite or vanadium zeolite powder prepared in this manner is then molded as described above for the purposes of the present invention.

Preferred titanium zeolites or vanadium zeolites are those having a pentasil zeolite structure, in particular the types assigned by X-ray diffraction to the BEA, MOR, TON, MTW, FER, MFI, MEL or MFI/MEL mixed structure. Zeolites of this type are described, for example, in W. M. Meier and D. H. Olson, Atlas of Zeolite Structure Types, Butterworth, 2nd Ed., London 1987. Titanium-containing zeolites having the ZSM-48, ZSM-12, ferrierite, β-zeolite or mordenite structure are also possible for the present invention.

The novel oxidation catalyst contains from 0.01 to 30, in partic- ular from 0.05 to 15, especially from 0.1 to 8, % by weight, based in each case on the amount of the titanium zeolites or vanadium zeolites, of the stated noble metals. Palladium is particularly preferred. The noble metals can be applied to the catalyst in the form of suitable noble metal components, for example in the form of water-soluble salts, before, during or after the compacting shaping step.

In many cases, however, it is most advantageous not to apply the noble metal components to the catalyst moldings under after the shaping step, particularly when a high-temperature treatment of the noble metal-containing catalyst is undesirable. The noble metal components can be applied to the molded catalyst in particular by ion exchange, impregnation or spraying on. The application may be effected by means of organic solvents, aqueous ammoniacal solutions or supercritical phases, such as carbon dioxide.

By using these abovementioned methods, it is quite possible to produce a very wide range of catalysts containing noble metals. Thus, a type of coated catalyst can be produced by spraying the noble metal solution onto the catalyst moldings. The thickness of this shell containing noble metal can be substantially increased by impregnation, whereas ion exchange results in the catalyst particles containing noble metal distributed substantially uniformly over the cross-section of the molding.

The novel molded oxidation catalyst is very useful for epoxidizing olefins by means of hydrogen and oxygen. The present invention therefore also relates to a process for the preparation of epoxides from olefins, hydrogen and oxygen, wherein the olefins are converted under heterogeneous catalysis using a novel oxidation catalyst.

The novel process for the preparation of epoxides can be carried out in principle by all conventional reaction procedures and in all conventional reactor types, for example by the suspension procedure or in a fixed-bed arrangement. Continuous or batchwise methods may be employed. However, the epoxidation is preferably carried out in a fixed-bed apparatus.

Depending on the olefin to be converted, the novel epoxidation can be carried out in the liquid phase, in the gas phase or in the supercritical phase, reaction of the olefins with the hydrogen/oxygen gas mixture in a liquid phase or a gas phase procedure being preferred.

If the novel epoxidation is carried out in the liquid phase, it is advantageous to operate at from 1 to 10 bar and in the presence of solvents. Suitable solvents are alcohols, eg. methanol, ethanol, isopropanol or tert-butanol or mixtures thereof, and in particular water. It is also possible to use mixtures of the stated alcohols with water. In certain cases, use of water or water-containing solvent systems substantially increases the selectivity of the desired epoxide compared with pure alcohols as solvents.

The novel epoxidation is carried out, as a rule, at from −20 to 70° C., in particular from −5 to 50° C. The molar ratio of hydrogen to oxygen $H_2:O_2$ can usually be varied in the range from 1:10 to 1:1 and is particularly advantageously from 1:5 to 1:1. The molar ratio of oxygen to olefin is as a rule from 1:4 to 1:10, preferably from 1:5 to 1:7. Any desired inert gas may be fed in as a carrier gas, nitrogen being particularly suitable.

The olefin used may be any desired organic compound which contains at least one ethylenically unsaturated double bond. It may be aliphatic, aromatic or cycloaliphatic and may consist of a linear or a branched structure. Preferably, the olefin contains 2 to 30 carbon atoms. More than one ethylenically unsaturated double bond may be present, this being the case, for example, in dienes or trienes. The olefin may additionally contain functional groups, such as halogen atoms, carboxyl groups, carboxylic ester functions, hydroxyl groups, ether bridges, sulfide bridges, carbonyl functions, cyano groups, nitro groups or amino groups.

Typical examples of such olefins are ethylene, propene, 1-butene, cis- and trans-2-butene, 1,3-butadiene, pentenes, isoprene, hexenes, octenes, nonenes, decenes, undecenes, dodecenes, cyclopentene, cyclohexene, dicyclopentadiene, methylenecyclopropane, vinylcyclohexane, vinylcyclohexene, allyl chloride, acrylic acid, methacrylic acid, crotonic acid, vinylacetic acid, allyl alcohol, alkyl acrylates, alkyl methacrylates, oleic acid, linoleic acid, linolenic acid, esters and glycerides of such unsaturated fatty acids, styrene, α-methylstyrene, divinylbenzene, indene and stilbene. Mixtures of the stated olefins may also be epoxidized by the novel process.

The novel process is particularly suitable for epoxidizing propene to give propylene oxide.

The novel molded oxidation catalysts have a number of advantages. As stated above, the oxidation catalysts have a high mass-specific activity, which furthermore does not substantially decrease in the course of time, and sufficient hardness and abrasion resistance, which makes them particularly interesting for use in fixed-bed apparatuses. Because the catalyst moldings have no fractions of small and very small particles which may have adverse influences due to retention effects, the spectrum of by-products and secondary products in the epoxidation is small and an associated reduction in activity with time is virtually undetectable.

Also advantageous is the small amount of binder required in the molded oxidation catalyst, ie. not more than 10% by weight; usually, such catalysts contain up to 20% by weight of binder. Such high binder contents do of course adversely affect the activity of the catalyst.

The examples which follow illustrate the preparation of the novel oxidation catalysts and the novel epoxidation without implying any restriction.

EXAMPLE 1

455 g of tetraethyl orthosilicate were initially taken in a 2 l four-necked flask and 15 g of tetraisopropyl orthotitanate were added through a dropping funnel in the course of 30 minutes while stirring (250 rpm, paddle stirrer). A colorless, clear mixture formed. Finally, 800 g of a 20% strength by weight tetrapropylammonium hydroxide solution (alkali content <10 ppm) were added and stirring was continued for a further hour. The alcohol mixture (about 450 g) formed as a result of the hydrolysis was distilled off at from 90 to 100° C. The mixture was made up with 1.5 l of deionized water and the now slightly opaque sol was introduced into a 2.5 l stainless steel stirred autoclave.

The closed autoclave (anchor stirrer, 200 rpm) was brought to a reaction temperature of 175° C. at a heating rate of 3°/min. After 92 hours, the reaction was complete. The cooled reaction mixture (white suspension) was centrifuged and the solid product was washed neutral with water. The solid obtained was dried at 110° C. for 24 hours (weight 149 g).

Finally, the template still remaining in the zeolite was removed by calcination under air at 550° C. in 5 hours (calcination loss: 14% by weight).

Wet chemical analysis showed that the pure white product had a Ti content of 1.5% by weight and a residual alkali content of less than 100 ppm. The yield was 97%, based on $SiO_2$ used. The crystallites measured 0.05–0.25 μm and the product showed a typical IR band at about 950 cm$^{-1}$.

EXAMPLE 2

1000 g of titanium silicalite from Example 1 were suspended in a mixture of 6 l of a 5% strength by weight sulfuric acid and 600 g of 30% strength by weight hydrogen peroxide solution and stirred at 80° C. for 2 hours. Thereafter, the titanium silicate treated in this manner was filtered off with suction and treated a further three times as described. The titanium silicalite was then suspended in 6 l of water, stirred at 80° C. for 2 hours and filtered off with suction. This process was repeated once. Thereafter, the solid treated in this manner was dried at 150° C. and then calcined at 500° C. for 5 hours under air.

EXAMPLE 3

950 g of titanium silicalite from Example 2 were suspended in 6 l of a 1% strength by weight sodium acetate solution in water and refluxed for 20 minutes, after which the titanium silicalite was filtered off with suction. This process was repeated twice more. The titanium silicalite treated in this manner was then suspended in 6 l of water, refluxed for 30 minutes and filtered off with suction. This process, too, was repeated. The titanium silicalite was then dried at 150° C. and calcined at 500° C.

EXAMPLE 4

100 g of titanium silicalite from Example 3 were dry-blended with 5 g of methylcellulose. This mixture was compacted in a kneader with the addition of 95 ml of water and processed at a mold pressure of 30 bar to give extrudates of 2 mm diameter. These extrudates were dried overnight at 110° C. and calcined for 5 hours at 500° C. The lateral compressive strength of the extrudates without a binder was 9.5 N.

EXAMPLE 5

100 g of titanium silicalite from Example 3 were dry-blended with 5 g of methylcellulose. This mixture was compacted in a kneader with the addition of 70 ml of water and 12.5 g of ammonium-stabilized silica sol (Ludox® AS-40, DuPont, 40% by weight of $SiO_2$) and processed at a mold pressure of 30 bar to give extrudates of 2 mm diameter. These extrudates were dried overnight at 110° C. and calcined for 5 hours at 500° C. The lateral compressive strength of the extrudates containing 4.8% by weight of binder was 22.5 N.

EXAMPLE 6

113 g of molded titanium silicalite according to Example 5 were introduced into a glass tube with incorporated glass frit and covered with glass wool. A solution of 3.8 g of $PdCl_2$ and 25% strength by weight aqueous ammonia solution was slowly circulated through this filled glass tube. After 24 hours, virtually all the palladium had been removed from the circulating liquid. The catalyst extrudates were then washed chloride-free with water in the glass tube. The catalyst extrudates treated in this manner were then dried at 60° C. under reduced pressure for 16 hours.

In a laboratory oven (quartz glass, diameter 10 cm, length of heating zone 20 cm), 50 g of the Pd-modified product were treated in the course of 90 minutes at 50° C. with a gas mixture comprising 20 l/h of nitrogen and 1 l/h of hydrogen at an oven speed of 50 rpm.

COMPARATIVE EXAMPLE A

To impregnate titanium silicalite powder from Example 3, a flesh-colored solution was first prepared with 0.515 g of palladium(II) chloride and 120 g of ammonia solution (25% strength by weight in water) with stirring at room temperature. In a round-bottomed flask, 60 g of the freshly prepared titanium silicalite from Example 3 were suspended in 130 g of demineralized water. The total amount of the prepared tetramine-chloro-palladium complex solution was added and stirring was carried out for 1 hour in a rotary evaporator at room temperature and atmospheric pressure. Finally, the suspension was evaporated down at from 90 to 100° C. under reduced pressure (from 5 to 19 mbar). The white product was used directly for the reduction.

In a laboratory oven (quartz glass, diameter 5 cm, length of heating zone 20 cm), 20 g of the Pd-modified product were reduced in the course of 90 minutes at 50° C. with a gas mixture comprising 20 l/h of nitrogen and 1 l/h of hydrogen at an oven speed of 50 rpm.

COMPARATIVE EXAMPLE B

In a pressure-resistant glass reactor, 2 g of catalyst from Comparative Example A were suspended, while stirring, in 1650 ml of methanol as solvent. At 60° C. and 5 bar, a gas mixture comprising 5 l/h of propene, 0.25 l/h of hydrogen, 1 l/h of oxygen and 0.5 l/h of nitrogen was then passed in. With an exit gas stream of 6.8 l, gas chromatographic analysis indicated 0.30% by volume of propylene oxide after 44 hours, 0.68% by volume of propylene oxide after 139 hours, 0.50% by volume of propylene oxide after 270 hours and 0.32% by volume of propylene oxide after 360 hours. This demonstrates a substantial decrease in activity in the course of the last 220 hours.

EXAMPLE 7

9.8 g of a catalyst from Example 6 were installed in a glass reactor and were flooded with a solvent stream of 4.5 kg/h of an aqueous methanol solution by an ascending method and the mixture was circulated. 6.2 l/h of propene, 1.2 l/h of oxygen and 0.3 l/h of hydrogen were metered into the 210 ml of solvent at the reactor inlet with pressure regulation at 5 bar. Concentrations of 0.11% by volume of propylene oxide were found in the exit gas over a duration of about 120 hours.

We claim:

1. An oxidation catalyst, comprising:
   a support of titanium silicalite or vanadium silicalite having a zeolite structure and from 0.01 to 30% by weight of one or more noble metals selected from the group consisting of ruthenium, rhodium, palladium, osmium, iridium, platinum, rhenium, gold and silver, and not more than 10% by weight, based on the total weight of the molded catalyst, of a binder, wherein the oxidation catalyst has been molded by a compacting shaping process and a minimum particle size of 0.5 mm.

2. An oxidation catalyst as claimed in claim 1, which has a particle diameter of 1 to 10 mm.

3. An oxidation catalyst as claimed in claim 1, comprising 0.1 to 7% by weight, based on the total weight of the molded catalyst, of a binder.

4. An oxidation catalyst as claimed in claim 3, wherein the binder, a compound of silicon, of aluminum, of boron, of phosphorus, of zirconium or of titanium.

5. An oxidation catalyst as claimed in claim 1, further comprising one or more elements selected from the group consisting of aluminum, boron, fluorine, zirconium, gallium, tin, iron, cobalt and nickel in the zeolite skeleton.

6. An oxidation catalyst as claimed in claim 1, having a molar ratio of titanium or vanadium to the sum of silicon and titanium or vanadium of 0.01:1 to 0.1:1.

7. An oxidation catalyst as claimed in claim 1, obtainable by applying the noble metals in the form of suitable noble metal components to the catalyst before, during or after the compacting shaping process.

8. A process for the preparation of an epoxide from an olefin, hydrogen and oxygen, comprising reacting the olefin, hydrogen and oxygen under heterogeneous catalysis in the presence of the oxidation catalyst as claimed in claim 1.

9. A process as claimed in claim 8, wherein the reaction is conducted in a fixed-bed apparatus.

10. A process as claimed in claim 8, for the preparation of propylene oxide from propene.

* * * * *

UNITED STATES PATENT AND TRADEMARK OFFICE
CERTIFICATE OF CORRECTION

PATENT NO. : 6,008,389

DATED : December 28, 1999

INVENTOR(S): Georg H. GROSCH, et al.

It is certified that an error appears in the above-identified patent and that said Letters Patent is hereby corrected as shown below:

On the Title Page, Item [54], and at the top of Column 1, the Title should read as follows:

[54] OXIDATION CATALYST AND PROCESS FOR THE PRODUCTION OF EPOXIDES FROM OLEFINS, HYDROGEN AND OXYGEN USING SAID OXIDATION CATALYST

Signed and Sealed this

Seventeenth Day of April, 2001

*Attest:*

NICHOLAS P. GODICI

*Attesting Officer*       Acting Director of the United States Patent and Trademark Office